United States Patent [19]

Rubino

[11] Patent Number: 5,688,951
[45] Date of Patent: Nov. 18, 1997

[54] HINDERED AMINE LIGHT STABILIZER

[75] Inventor: Mark R. Rubino, Pittsburgh, Pa.

[73] Assignee: Aristech Chemical Corp, Pittsburgh, Pa.

[21] Appl. No.: 613,898

[22] Filed: Mar. 11, 1996

[51] Int. Cl.⁶ .................. C07D 211/14; C07D 211/70; C08K 5/34; C08K 5/35
[52] U.S. Cl. .................. 546/184; 524/99; 524/100; 524/102; 546/255; 546/350
[58] Field of Search .................. 546/184, 255, 546/350; 524/99, 100, 102

[56] References Cited

U.S. PATENT DOCUMENTS

| | | | |
|---|---|---|---|
| 3,502,725 | 3/1970 | Dewhirst | 260/577 |
| 3,652,614 | 3/1972 | Dewhirst | 260/429 |
| 3,939,170 | 2/1976 | Randell | 260/294.8 F |
| 3,975,357 | 8/1976 | Murayama | 260/45.8 N |
| 4,960,593 | 10/1990 | Sevini | 524/99 |
| 5,206,396 | 4/1993 | Gruber | 554/27 |
| 5,236,909 | 8/1993 | Gruber | 514/53 |

Primary Examiner—C. Warren Ivy
Assistant Examiner—Evelyn Huang
Attorney, Agent, or Firm—William L. Krayer

[57] ABSTRACT

New N-substituted piperidines useful as light stabilizers in synthetic resins are disclosed. They are 1-(2,7-octadienyl)-2,2,6,6-tetraalkylpiperidines wherein the alkyl groups are independently selected lower alkyl groups such as methyl or ethyl and the 3 and 5 positions may be substituted by methyls. The ring may be monounsaturated; a new compound 1-(2,7-octadienyl)-2, 2,6,6-tetramethyl-3-pyridine is described.

5 Claims, No Drawings

HINDERED AMINE LIGHT STABILIZER

TECHNICAL FIELD

This invention relates to new compounds useful as light stabilizers in synthetic resins. They may also be used to contribute heat and light stability to other materials and blends. In particular, the invention describes tetraalkyl piperidines and partially hydrogenated pyridines substituted with an octadienyl group at the 1-position.

BACKGROUND OF THE INVENTION

In U.S. Pat. No. 3,975,357, Murayama et al describe (Referential Example 1, beginning at line 67 of column 17) the synthesis of 1-octyl-2,2,6,6-tetramethylpiperidine by the reaction of 2,2,6,6-tetramethylpiperidine with 1-bromooctane. They also suggest the formation of 1-n-dodecyl-2,2,6,6-tetramethylpiperidine if 1-bromododecane is substituted for the 1-bromooctane.

Octadienyl piperidine, having no alkyl groups on carbons of the piperidine ring and therefore not a hindered amine, is also known—see U.S. Pat. No. 5,118,837. Several workers have made octadienyl piperidine by reacting piperidine with butadiene and catalyst: GB patent 1,535,718; U.S. Pat. No. 4,104,471; DD 129,779; Chem Abstr 112:178603.

Octadienyl groups have been placed at the 4-position of a hindered piperidine group by reaction of 4-hydroxy-2,2,6,6-tetramethylpiperidine with butadiene in the presence of a catalyst to produce 2,2,6,6-tetramethyl-4-(2,7-octadienyloxy)piperidine—see U.S. Pat. Nos. 5,206,396 and 5,236,909.

Generally, workers who have attempted to make 1-octadienyl piperidines using butadiene have said that the reaction will not proceed with hindered piperidines, i.e. those having full substitution in the 2 and 6 positions. This observation seems to be borne out by the results in the patents just mentioned, where the hindered nitrogen was apparently inert while the alkylation proceeded at the 4-position. Thus I am not aware of the existence of the particular class of compounds with which this invention is concerned, tetraalkyl piperidines substituted with an octadienyl group at the 1-position.

Monounsaturated alkylene groups are seen to be in the 1-position in some of the hindered piperidine groups described by Sevini et al in U.S. Pat. No. 4,960,593. Neither of these describes di-unsaturated groups such as are placed herein on the nitrogen of fully hindered piperidines.

SUMMARY OF THE INVENTION

My new compounds are 1-(2,7-octadienyl)-2,2,6,6-tetraalkylpiperidines of the formula

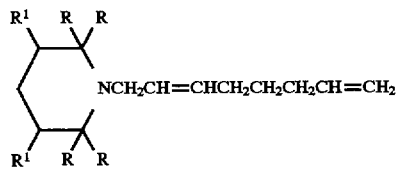

where each R is independently selected from alkyl groups having from one to two carbon atoms and each $R^1$ is independently H or $CH_3$, provided that the ring may be monounsaturated, in which case the compounds are 1-(2,7-octadienyl)-2,2,6,6-tetraalkyl-1,2,5,6-tetrahydropyridines of the formula

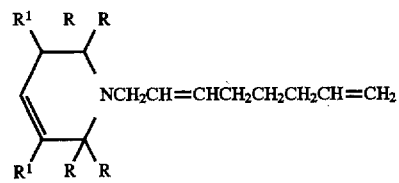

DETAILED DESCRIPTION OF THE INVENTION

Preparation of 1-(2,7-octadienyl)-2,2,6,6-tetramethylpiperidine:

Part A. Chlorooctadiene was prepared from 2,7-octadien-1-ol using thionyl chloride according to J. Tsuji, K. Mizutani, I. Shimizu and K. Yamamoto: Chemistry Letters 1976, 773–774.

Part B. N-methylpyrrolidinone (406 g, $H_2O$ <0.05%) and 2,2,6,6-tetramethylpiperidine (383.6 g, 99.5% by gc, 2.70 mole) were stirred at 60° C. and atmospheric pressure under argon. Granular potassium iodide (37.4 g, 0.225 mole) was gradually added. Distilled chlorooctadiene (110.7 g, 0.765 mole) was added and the mixture was stirred at 60°–80° C. for twelve hours. The mixture was cooled to 25° C. and combined with 50% aqueous sodium hydroxide (85 g, 1.06 mole). Water (400 ml) and hexane (400 ml) were added and the mixture was well agitated. The lower aqueous layer was removed and the hexane was extracted with water (4×50 ml). The hexane layer was concentrated at reduced pressure on a rotary evaporator and then short-path distilled. After removing a forecut the product distilled at 89°–101° C. at 0.5 mm Hg. The liquid distillate was 98% pure by gc.

Corresponding octadienyl compounds having alkyl substitutions in the 2 and 6 positions on the piperidinyl group other than methyl, such as ethyl, can be made in a similar manner by using the desired 2,6 substituted piperidines in the preparation.

The new compounds are useful as light stabilizers in synthetic resins.

I claim:

1. A compound of the formula

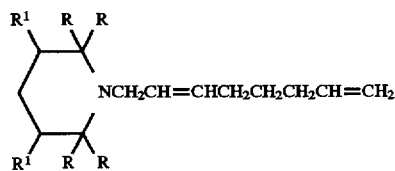

wherein each R is independently selected from alkyl groups having from one to two carbon atoms and each $R^1$ is H or $CH_3$.

2. 1-(2,7-octadienyl)-2,2,6,6-tetramethylpiperidine.

3. Compound of claim 1 wherein each $R^1$ is $CH_3$.

4. A compound of the formula
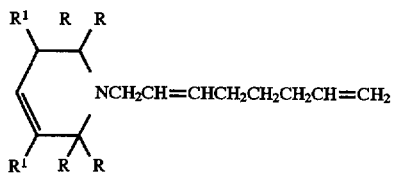
where each R is independently selected from alkyl groups having from one to two carbon atoms and $R^1$ is H or $CH_3$.
5. Compound of claim 4 wherein R is $CH_3$ and $R^1$ is H.
* * * * *